United States Patent [19]

Tepic

[11] 4,318,191
[45] Mar. 9, 1982

[54] COMPLIANT HEAD FEMORAL ENDOPROSTHESIS

[75] Inventor: Slobodan Tepic, Cambridge, Mass.

[73] Assignee: Massachusetts Institute of Technology, Cambridge, Mass.

[21] Appl. No.: 177,657

[22] Filed: Aug. 13, 1980

[51] Int. Cl.³ .................................................. A61F 1/24
[52] U.S. Cl. ................................. 3/1.913; 128/92 CA
[58] Field of Search .................... 3/1.913, 1.912, 1.91, 3/1.9; 128/92 C, 92 CA

[56] References Cited

U.S. PATENT DOCUMENTS

| 3,064,645 | 11/1962 | Ficat et al. | 128/92 CA |
| 3,648,294 | 3/1972 | Shahrestani | 3/1.912 |
| 3,813,699 | 6/1974 | Giliberty | 3/1.913 |
| 3,896,505 | 7/1975 | Timmermans | 3/1.913 |
| 4,032,994 | 7/1977 | Frey | 3/1.912 |

FOREIGN PATENT DOCUMENTS

| 2015324 | 11/1971 | Fed. Rep. of Germany | 3/1.913 |
| 2297030 | 8/1976 | France | 3/1.912 |

*Primary Examiner*—Ronald L. Frinks
*Attorney, Agent, or Firm*—Arthur A. Smith, Jr.; Paul J. Cook

[57] ABSTRACT

An endoprosthesis is provided which includes a femoral head construction having a compliant metal shell attached thereto. The shell fits into the acetabulum of the hip joint and is spaced apart from a spherical surface of the construction a sufficient distance to permit the shell to flex without exceeding its elastic limit.

3 Claims, 6 Drawing Figures

COMPLIANT HEAD FEMORAL ENDOPROSTHESIS

The Government has rights in this invention under Grant No. AM-16116 awarded by the National Institute of Health.

BACKGROUND OF THE INVENTION

This invention relates to a hip joint prosthesis. More particularly, this invention relates to an endoprosthesis having a compliant head that conforms to the shape of the acetabulum of the patient.

Replacement of diseased or otherwise impaired natural joints of the human skeleton or their components by artificial prosthetic devices has gained an extremely wide acceptance in the field of orthopaedics. Endoprostheses generally have a stiff spherical or slightly out-of-round head. All attempts to produce a soft endoprosthesis using plastic materials have been unsuccessful.

The hip joint is a ball and socket joint of the type required to allow rotation about all three axes. While it is clear that two spherical surfaces satisfy the requirement of three axes of rotation, and both the femoral head and the acetabulum of the hip joint appear to be quite spherical when unloaded, it is not clear that these unloaded shapes are maintained under load, particularly so because of the variations in thickness of the two cartilage layers.

Presently available measurement techniques have determined that the cartilage surface of the acetabulum is very spherical with maximum deviations from sphericity on the order of about 150 $\mu$m and that the surface of the underlying bone of the acetabulum is spherical to within about 500 $\mu$m. In addition, these measurements show that the cartilage surface of the femoral head is very spherical with maximum deviations of about 200 $\mu$m occurring on very localized areas adjacent to the cartilage edges and over most of the surface being less than about 100 $\mu$m while the maximum deviations from sphericity of the femoral bone surface are on the order of about 500 $\mu$m. As is well known in anatomy, the cartilage thickness distribution on the femoral head and on the acetabulum are reciprocal in the sense that a thicker cartilage on the acetabulum corresponds (in erect posture) to thinner cartilage on the femoral head. As the first approximation, local compliancy of the cartilage layer can be considered proportional to its local thickness. Most of the thickness variation can be accounted for by the relative shift of the best-fitting spheres to the cartilage surface and to the cartilage-to-bone interface. Consistency of this shift suggests physiological significance of the cartilage thickness distribution.

Accordingly, it would be desirable to provide an endoprosthesis that approaches the compliancy of the natural femoral head as nearly as possible both in the magnitude and distribution. In addition, it would be desirable to provide such an endoprosthesis which is, by adjusting its shape under the normal load to which the joint is subjected, capable of compensating for unavoidable errors in choosing the proper size of the replacement.

SUMMARY OF THE INVENTION

The present invention provides an endoprosthesis comprising a stiff spherical head having attached thereto a compliant shell approximating the size and shape of a natural femoral head. The shell is formed from a metal and is spaced apart from the stiff spherical head so that, when positioned in the hip joint, it is capable of being deflected to correspond to the shape of the acetabulum cartilage. The stiff spherical head limits the deflection of the compliant shell. The stiff spherical head and compliant shell are attached to a stem which fits into the thigh bone.

DESCRIPTION OF SPECIFIC EMBODIMENTS

The present invention comprises an endoprosthesis including a stiff head formed from a metal and which has a spherical shape as well as means for being attached to a stem which, in turn, is implanted in the thigh bone. To the portion of the outer surface of the stiff head which would normally contact the acetabulum is attached a flexible metal shell which is sufficiently flexible to conform to the contacting surface of the acetabulum's cartilage and which is sufficiently strong so that it remains intact during use. The major portion of the shell is spaced apart from the femoral head a distance to permit the shell to flex during use but not so far a distance that its elastic limit is exceeded during use. That is to say, the outer surface of the stiff head controls the limit of deflection of the shell attached thereto. In one embodiment a viscoelastic material can be positioned between the inner surface of the shell and the outer surface of the stiff head in order to further regulate flexing of the shell and to permit more accurate conformance with the cartilage of the acetabulum.

Figure 1:
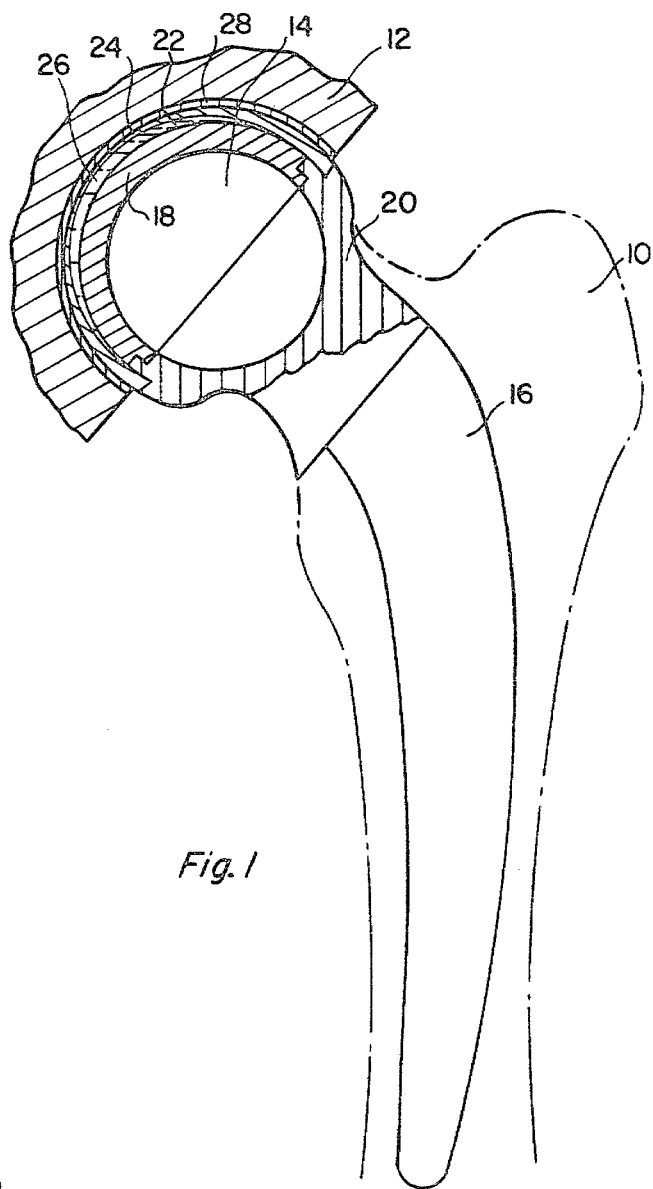
FIG. 1 is a partial cross-sectional view of the prosthesis of this invention.

Referring to the figures, FIG. 1 shows the upper end of the femur 10 and the pelvis 12. The endoprosthesis includes a head indicated generally as 14 and a stem 16 attached to the femoral head 14 and which extends into the femur 10. The femoral head 14 includes a top section 18 which is attached to the top portion 20 of the stem 16. The outer surface 22 of the top section 18 of the femoral head is spherical. A resilient or compliant metal shell 24 is secured to top section 20 of the stem 16 such as be being cemented thereto. The compliant shell 24 is spaced apart from the spherical surface 22 to leave a space 26 therebetween. The space 26 allows the compliant shell 24 to flex so that it conforms to the shape of the acetabulum cartilage 28 so that the cartilage 28 and the compliant shell 24 are essentially congruent. Generally, the compliant shell 24 and the spherical surface 22 are spaced apart from each other between about 0.0005 and about 0.010 inches. This permits the compliant shell 24 to flex when loaded without exceeding its elastic limit.

Figure 2:
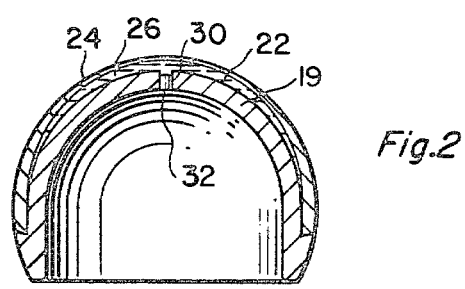
FIG. 2 shows an alternative embodiment of this invention utilizing a viscoelastic layer on a femoral head resurfacing cup.

FIG. 2 shows a modified version of the femoral head of FIG. 1. The spherical surface 22 of the femoral resurfacing cup 19, is provided with a bore 30. The space 26 between the compliant shell 24 and the spherical surface 22 is provided with a viscoelastic material such as a silicone polymer or the like. After the space 26 has been filled, a plug 32 is inserted into the bore 30 so that the viscoelastic material is retained in space 26. The viscoelastic material provides a means for dampening sudden forces on the compliant shell which thereby further minimizes the chance of damaging the shell due to sudden loads thereon.

Figure 3:
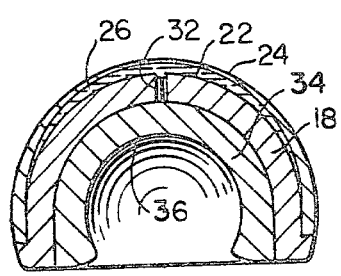
FIG. 3 shows an alternative embodiment of this invention wherein the femoral head is attached to the stem by means of a spherical bearing.

Referring to FIG. 3, a femoral head construction is shown which includes a compliant shell 24, a spherical surface 22 on femoral head 18, a viscoelastic material within space 26, a plug 32 and a cup 34 having an inner surface 36 in order to accommodate a stem construction (not shown), the top portion of which includes a spherical ball adapted to fit into and to articulate with the cup surface 36.

Figure 4:
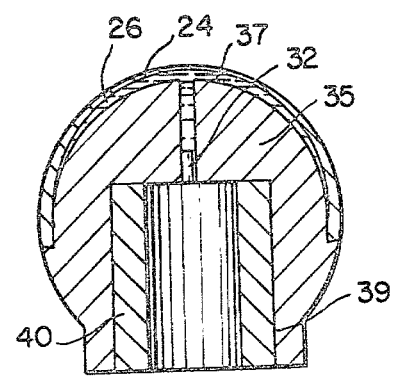
FIG. 4 shows an alternative embodiment of this invention utilizing a cylindrical bearing on the stem.

The construction shown in FIG. 4 also includes a compliant shell 24, a viscoelastic material within space 26 and a plug 32. The femoral head 35 has a spherical surface 37 and a cylindrical bore 39 into which is fit a cylinder 40 attached to a stem (not shown) which fits into a thigh bone.

Figure 5:
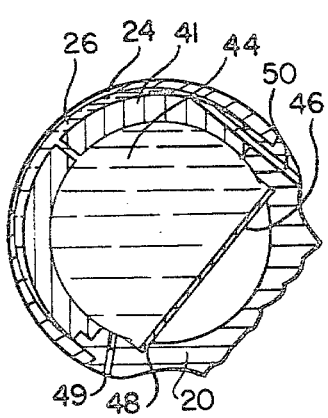
FIG. 5 shows an alternative embodiment of this invention using a dampening liquid.

As shown in FIG. 5, the femoral head 41 includes a compliant shell 24 and a viscous liquid within space 26 and space 44. The viscous liquid is held within these spaces by means of flexible membrane 46 which is welded to the interior surface 48 of the top section 20 of the stem. Ports 49 and 50 are provided for filling spaces 26 and 44 with the viscous liquid. After the filling is completed, the ports 49 and 50 are plugged.

Figure 6:
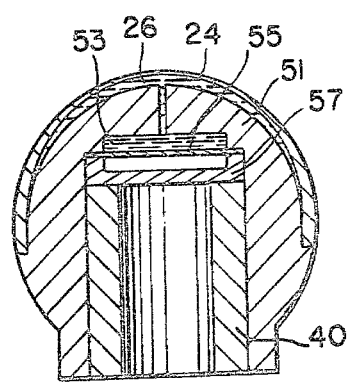
FIG. 6 shows an alternative embodiment of this invention utilizing a dampening liquid and a cylindrical bearing on the stem.

Referring to FIG. 6, the femoral head 51 includes compliant shell 24 and a viscous liquid which fills spaces 26 and 53. The viscous liquid is retained by means of flexible membrane 55 which is secured to the interior of femoral head 51 by means of plate 57 which is held in place by a cylindrical member 40.

It is to be understood that the present invention is not limited to the embodiments specifically described above, but includes these embodiments as well as obvious alternative embodiments thereto. Thus, it is not a requirement that the femoral head to which the compliant shell is attached be perfectly spherical. All that is necessary is that the shape of the femoral head not adversely affect the ability of the compliant shell to conform to the shape of the acetabulum cartilage.

I claim:

1. An endoprosthesis comprising a stem adapted to be secured to a thigh bone, a femoral head construction secured to said stem and adapted to fit into the acetabulum of a hip joint, said femoral head construction comprising an upper femoral head portion having an outside generally spherical shape, a compliant metal shell secured to and spaced away from said upper femoral head portion in order to cover said generally spherical surface, said compliant shell being spaced apart from said spherical surface at a distance to permit said compliant shell to flex within said acetabulum without exceeding its elastic limit.

2. The prosthesis of claim 1 wherein a viscoelastic material is positioned within the space between said compliant shell and said spherical surface.

3. The prosthesis of claim 1 wherein said upper femoral head portion is hollow and a viscous liquid is positioned within said hollow portion and within the space between said compliant shell and said spherical surface.

* * * * *